US008857803B2

(12) United States Patent
Schaper, Jr. et al.

(10) Patent No.: US 8,857,803 B2
(45) Date of Patent: Oct. 14, 2014

(54) DEVICES AND METHODS FOR HOLDING AN INTRAOCULAR LENS DURING THE PROCESSING AND PACKAGING OF THE INTRAOCULAR LENS

(75) Inventors: Dale T. Schaper, Jr., Lakeside, TX (US); Christopher E. Redman, Arlington, TX (US); Douglas Wensrich, Bedford, TX (US)

(73) Assignee: Novartis AG, Basel (CH)

( * ) Notice: Subject to any disclaimer, the term of this patent is extended or adjusted under 35 U.S.C. 154(b) by 620 days.

(21) Appl. No.: 12/945,184

(22) Filed: Nov. 12, 2010

(65) Prior Publication Data

US 2011/0140333 A1    Jun. 16, 2011

Related U.S. Application Data

(60) Provisional application No. 61/286,203, filed on Dec. 14, 2009.

(51) Int. Cl.
*B25B 1/24* (2006.01)
*A61F 2/16* (2006.01)

(52) U.S. Cl.
CPC .................................. *A61F 2/1691* (2013.01)
USPC ............................................ 269/86; 269/286

(58) Field of Classification Search
CPC ........ B25B 1/2484; B25B 1/103; B25B 5/08; B25B 1/08; B23Q 1/52; B23Q 1/54; A47J 43/28; B41F 15/0872; B41F 15/30
USPC ........... 269/286, 43, 45, 95, 289 R, 302.1, 86
See application file for complete search history.

(56) References Cited

U.S. PATENT DOCUMENTS

| 3,586,012 | A | 6/1971 | Paule |
| 3,614,959 | A | 10/1971 | Schollmaier et al. |
| 3,621,855 | A | 11/1971 | Rabinowitz |
| 4,113,088 | A | 9/1978 | Binkhorst |
| 4,254,509 | A | 3/1981 | Tennant |

(Continued)

FOREIGN PATENT DOCUMENTS

| EP | 0136807 B1 | 12/1990 |
| WO | 2011/075249 A1 | 6/2011 |

OTHER PUBLICATIONS

International Searching Authority, International Search Report, PCT/US2010/056490, Jan. 18, 2011, 2 pages.

(Continued)

*Primary Examiner* — Lee D Wilson

(57) ABSTRACT

A holder for an intraocular lens during the processing and packaging of the intraocular lens. The holder having an upper member having a base portion extending from the upper member along a first longitudinal axis. Additionally, the holder has a lower member having a receiving member defining a cavity for receiving the intraocular lens and a coupling member for engaging the base portion. The receiving member extending from the lower member along a second longitudinal axis and having at least one channel extending substantially through the receiving member that is substantially transverse to the second longitudinal axis. The holder has a locked position such that the upper and lower members are locked with respect to each other and at least one channel provides unobstructed access into the cavity of the receiving member for obtaining dimensional and optical measurements of the intraocular lens when the holder is in the locked position.

20 Claims, 8 Drawing Sheets

(56) References Cited

U.S. PATENT DOCUMENTS

| | | | |
|---|---|---|---|
| 4,257,521 A | 3/1981 | Poler | |
| 4,326,306 A | 4/1982 | Poler | |
| 4,369,355 A | 1/1983 | Helixon | |
| 4,423,809 A | 1/1984 | Mazzocco | |
| 4,444,307 A | 4/1984 | Jermyn | |
| 4,527,294 A | 7/1985 | Heslin | |
| 4,573,998 A | 3/1986 | Mazzocco | |
| 4,586,930 A | 5/1986 | Kelman | |
| 4,615,703 A | 10/1986 | Callahan et al. | |
| 4,697,697 A | 10/1987 | Graham et al. | |
| 4,738,355 A | 4/1988 | Jobe | |
| 4,775,121 A * | 10/1988 | Carty | 248/68.1 |
| 4,897,981 A | 2/1990 | Beck | |
| 5,127,517 A | 7/1992 | Clements et al. | |
| 5,337,888 A | 8/1994 | Morrison | |
| 5,407,062 A | 4/1995 | Shannon et al. | |
| D360,068 S | 7/1995 | Hambleton et al. | |
| 5,501,436 A * | 3/1996 | Miller | 269/47 |
| D382,399 S | 8/1997 | Hambleton et al. | |
| 5,788,225 A * | 8/1998 | Iwata et al. | 269/309 |
| 6,003,851 A * | 12/1999 | Araki et al. | 269/239 |
| 6,537,283 B2 | 3/2003 | Van Noy | |
| 6,578,246 B2 * | 6/2003 | Chen | 29/239 |
| 6,868,963 B2 | 3/2005 | Borovsky | |
| 7,144,003 B1 * | 12/2006 | Meade | 269/43 |
| 7,281,699 B2 | 10/2007 | Hovey et al. | |
| 2006/0049569 A1 * | 3/2006 | Yonezawa | 269/309 |
| 2008/0051801 A1 | 2/2008 | Hovey et al. | |
| 2011/0140333 A1 * | 6/2011 | Schaper et al. | 269/86 |

OTHER PUBLICATIONS

International Searching Authority, Written Opinion of the International Searching Authority, PCT/US2010/056490, Jan. 18, 2011, 6 pages.

Applicant's Prior Art Statement, submitted Dec. 4, 2013 (5 pages).

* cited by examiner

DEVICES AND METHODS FOR HOLDING AN INTRAOCULAR LENS DURING THE PROCESSING AND PACKAGING OF THE INTRAOCULAR LENS

This application claims priority to U.S. Provisional Application No. 61/286,203 filed Dec. 14, 2009.

BACKGROUND OF THE INVENTION

There continues to be a need for intraocular lens holders that support and protect the lens during the manufacturing process. The process of manufacturing an intraocular lens involves many complex manufacturing steps. For example, the lens may undergo polishing and/or cleaning during manufacturing of the lens. These steps of the manufacturing process provide an opportunity for the lens to be contacted and/or for particulate to accumulate near the lens, both of which, can cause damage to the lens. In that regard, the less a lens is touched during processing of the lens the better. Accordingly, for some applications it is desirable for a lens holder to be able to support and protect the lens from various particulate during the manufacturing of the lens while minimizing the touching of the lens.

Additionally, many in-process optical and dimensional measurements of the lens are taken at various progression points during the manufacturing of the lens. These measurements are taken to ensure that the lens being manufactured meets specified design requirements. Because of the precise nature of these measurements, the lens should be unobstructed from view and the lens should be held stationary to ensure that the various optical and dimensional measurements taken of the lens are accurate. Accordingly, for most applications it is desirable for a lens holder to hold the lens stationary, but also maintain pathways accessible during the manufacturing process that allow for performing optical and dimensional measurements of the lens.

Furthermore, potential damage to a lens can occur when the lens is transferred from a lens holder used during manufacturing to another lens holder that is used for packaging and shipping the lens to an end user (e.g. healthcare provider). Accordingly, it is desirable in some instances to have the same holder used during manufacturing to be usable for packaging purposes in order to simplify and reduce potential damage that might occur by transferring the lens to another holder for packaging and shipping purposes.

Accordingly, improved devices and methods for holding an intraocular lens during the processing and packaging of the lens are needed.

SUMMARY OF THE INVENTION

These and other aspects, forms, objects, features, and benefits of the present invention will become apparent from the following detailed drawings and description.

A holder for an intraocular lens. The holder having an upper member having a base portion extending from the upper member along a first longitudinal axis. Additionally, the holder has a lower member having a receiving member defining a cavity for receiving the intraocular lens and a coupling member for engaging the base portion. The receiving member extending from the lower member along a second longitudinal axis and having at least one channel extending substantially through the receiving member that is substantially transverse to the second longitudinal axis. The holder has a locked position such that the upper and lower members are locked with respect to each other and the at least one channel provides unobstructed access into the cavity of the receiving member for obtaining a dimensional measurement of the intraocular lens when the holder is in the locked position.

A further holder for an intraocular lens. The holder having an upper member having a base portion extending from the upper member along a first longitudinal axis. The base portion including at least one projection extending substantially transverse to the first longitudinal axis. The holder additionally having a lower member having a receiving member defining a cavity for receiving the intraocular lens and a coupling member for engaging the base portion. The receiving member extending from the lower member along a second longitudinal axis and having a first and second channel extending substantially through the receiving member that are substantially transverse to the second longitudinal axis. The coupling member having at least one recess for receiving the projection to lock and unlock the upper and lower members with respect to each other. When the upper and lower members are locked with respect to each other the first channel provides unobstructed access into the cavity of the receiving member for obtaining a dimensional measurement of a lens optics of the intraocular lens and the second channel provides unobstructed access into the cavity of the receiving member for obtaining a dimensional measurement of a haptic of the intraocular lens.

A method of processing an intraocular lens. The method including providing a lens holder. The lens holder having an upper member having a base portion. Also, the lens holder has a lower member having a receiving member defining a cavity for receiving the intraocular lens and a coupling member to engage the base portion. The receiving member extending from the lower member along a longitudinal axis and having a first and second channels extending substantially through the receiving member that are substantially transverse to the longitudinal axis. Furthermore, the method includes positioning the intraocular lens within a cavity of the lens holder. The method may also include performing a manufacturing process on the intraocular lens positioned within the lens holder. The method includes performing a dimensional measurement on the intraocular lens positioned within the lens holder through the first and second channels of the lens holder. In a further aspect, the method of processing the intraocular lens occurs without removal of the intraocular lens from the holder.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify the embodiments of this invention.

DETAILED DESCRIPTION OF THE INVENTION

Figure 1:
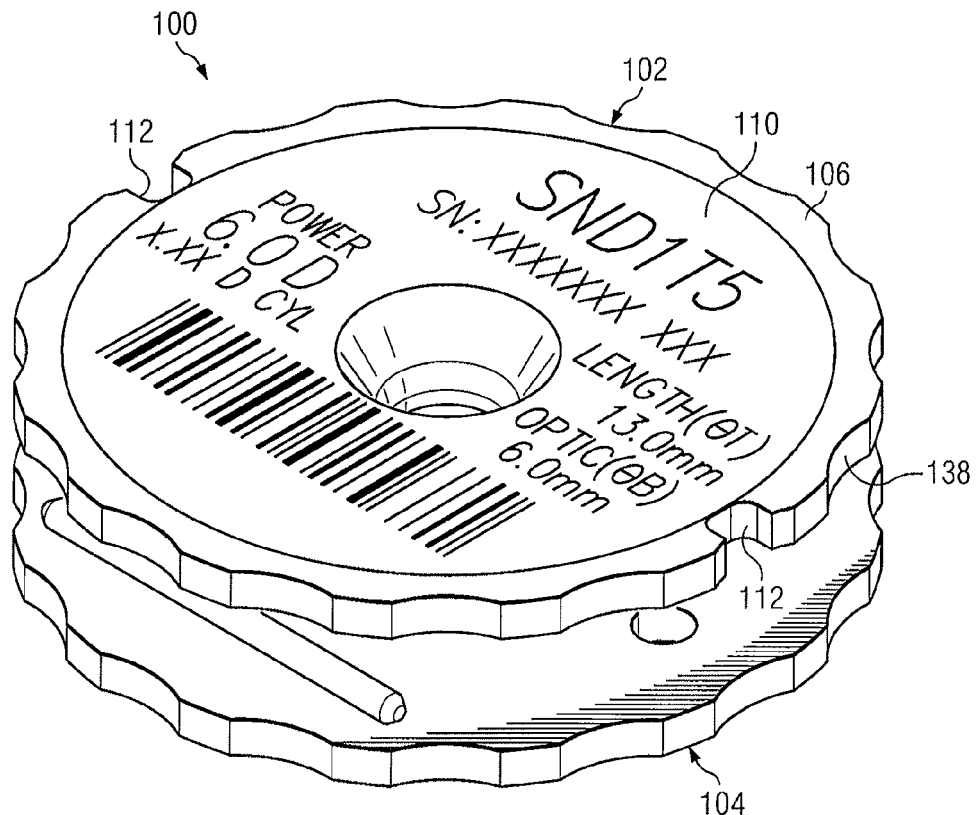
FIG. 1 is a perspective view of a lens holder for processing and packaging an intraocular lens according to one embodiment of the present disclosure.

The present disclosure relates generally to the field of ophthalmic surgery, and more particularly to devices and methods for holding an intraocular lens during the processing and packaging of the lens. For the purposes of promoting an understanding of the principles of the invention, reference will now be made to embodiments or examples illustrated in the drawings, and specific language will be used to describe these examples. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

Figure 2:
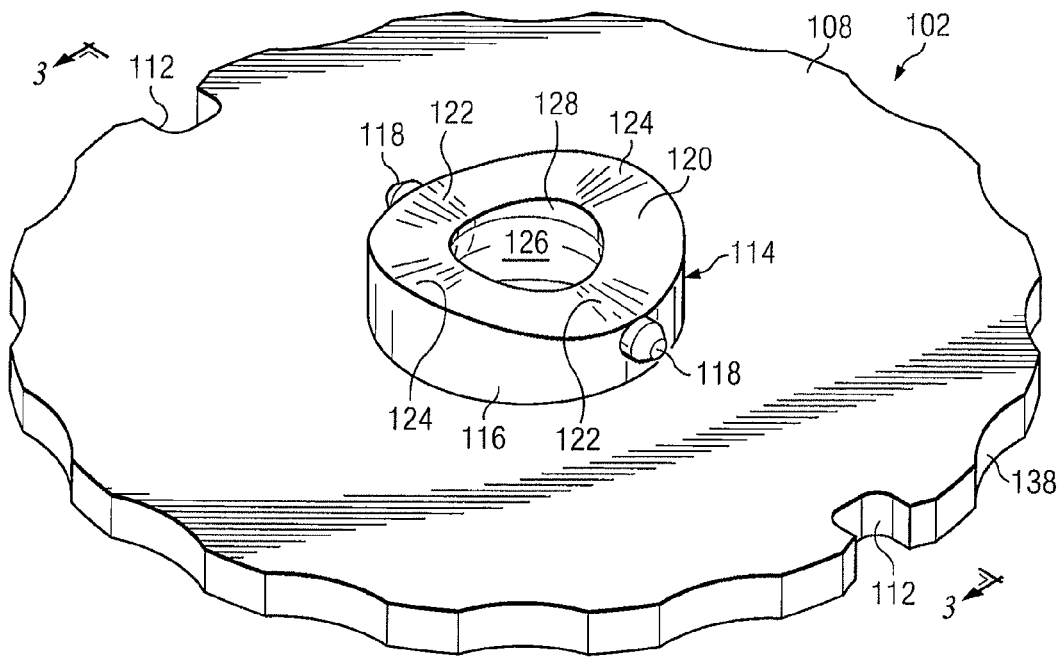
FIG. 2 is a perspective view of an upper member of the lens holder of FIG. 1.
Figure 3:
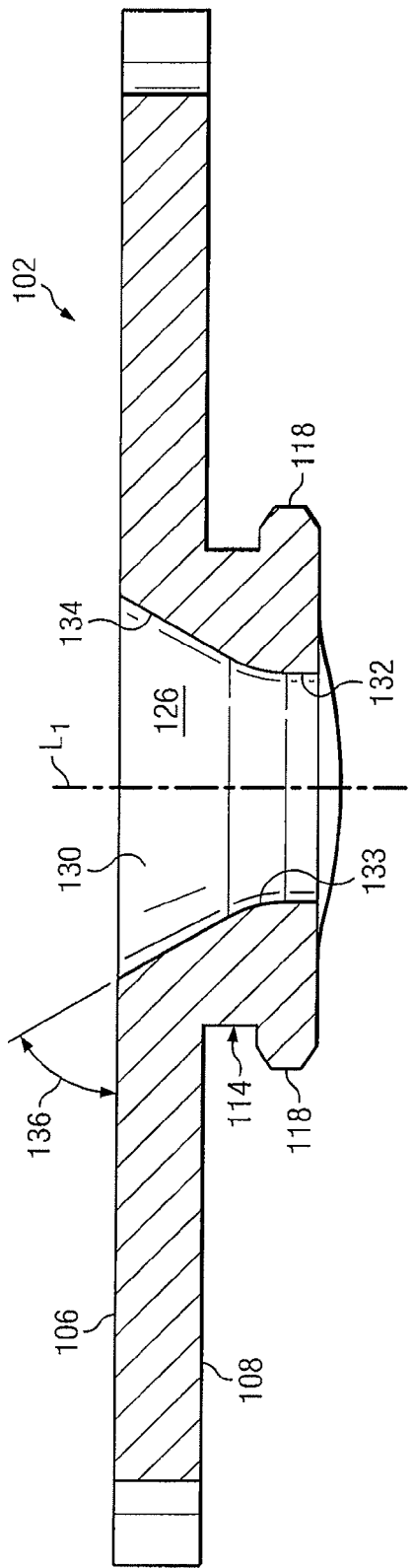
FIG. 3 is a cross-section view of a side view of the upper member of FIG. 2.
Figure 5:
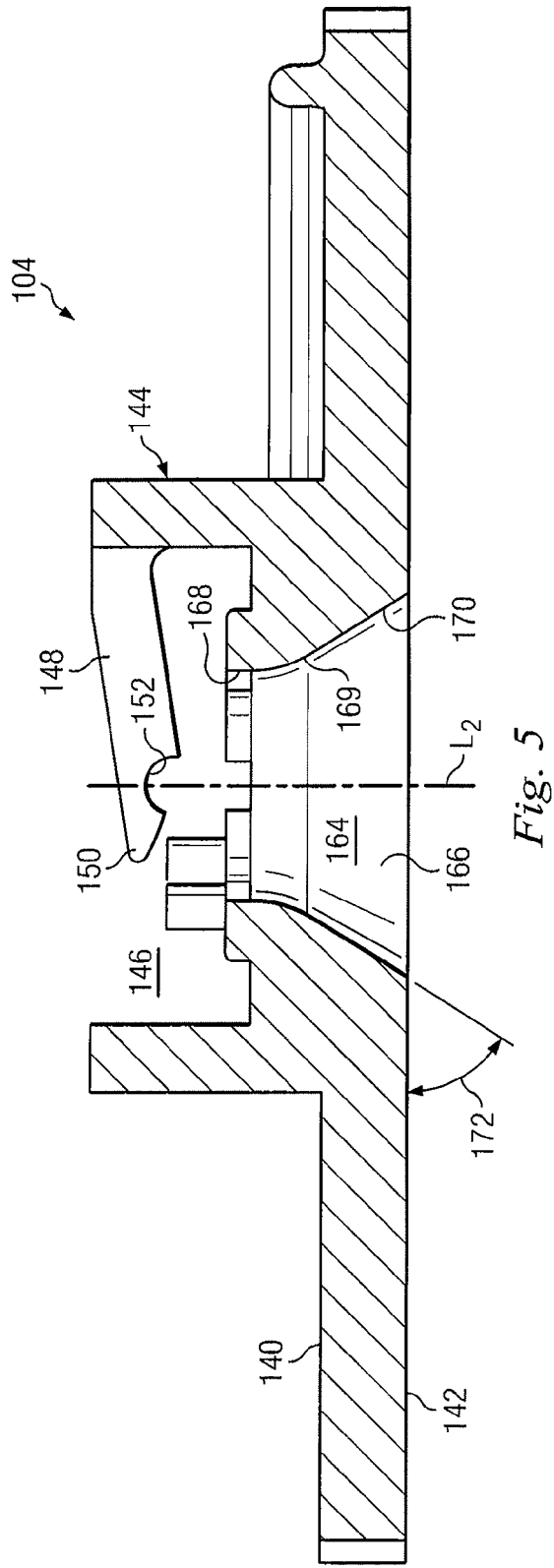
FIG. 5 is a cross-section view of a side view of the lower member of FIG. 4.
Figure 4:
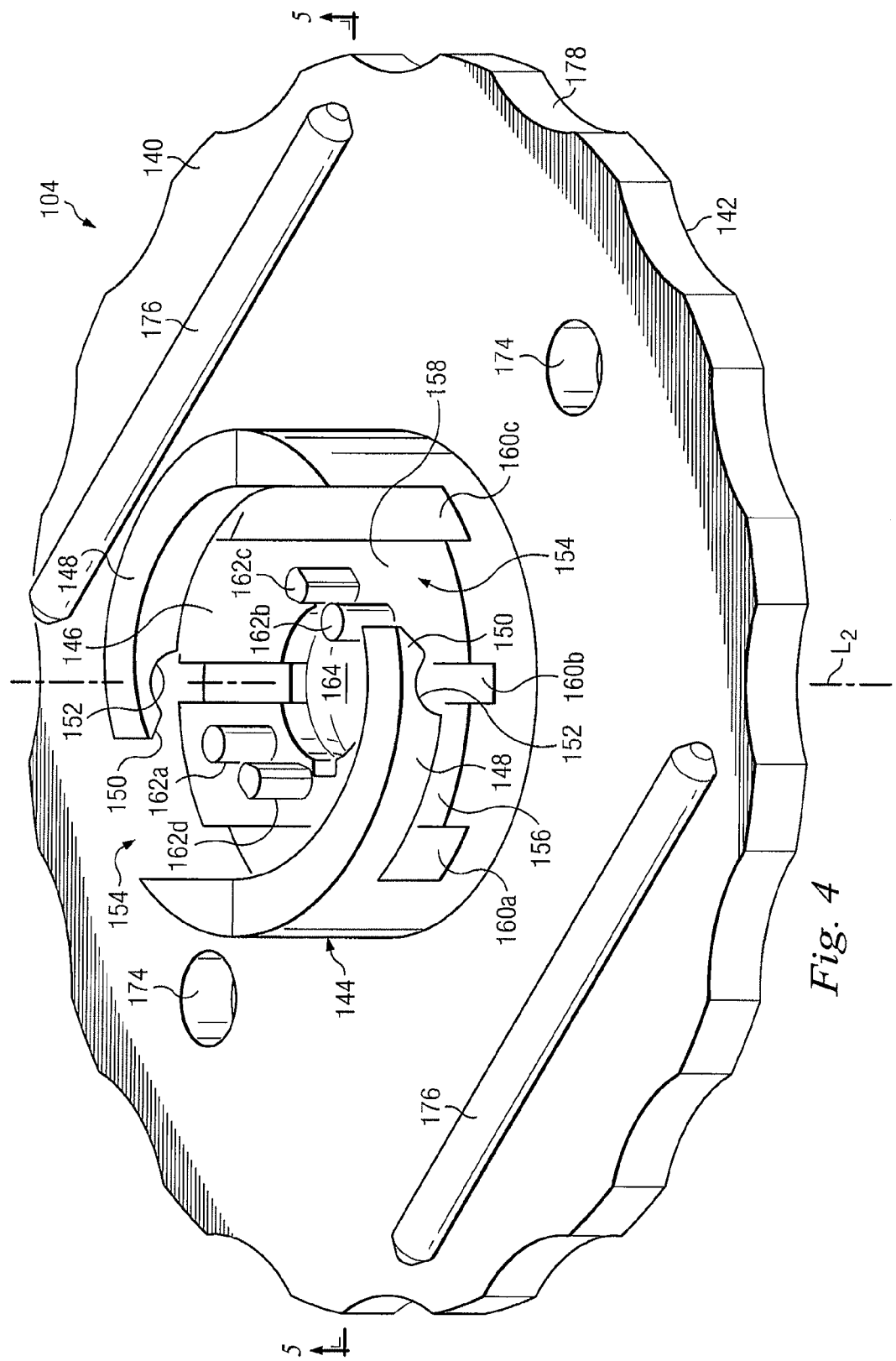
FIG. 4 is a perspective view of a lower member of the lens holder of FIG. 1.

FIGS. 1-5 show various views of an exemplary embodiment of a lens holder for holding an intraocular lens. FIG. 1 is a perspective view of a lens holder for processing and packaging an intraocular lens according to one embodiment of the present disclosure. FIG. 2 is a perspective view of an upper member of the lens holder of FIG. 1. FIG. 3 is a cross-section view of a side view of the upper member of FIG. 2. FIG. 4 is a perspective view of a lower member of the lens holder of FIG. 1. FIG. 5 is a cross-section view of a side view of the lower member of FIG. 4.

Referring first to FIG. 1, a perspective view of a lens holder 100 for holding an intraocular lens is shown. Lens holder 100 is formed of an upper member 102 and a lower member 104. Upper member 102 has an upper surface 106 and an opposing lower surface 108 (see FIG. 2). As shown, upper surface 106 can have indicia 110 that provide information relating to an intraocular lens being held by the lens holder 100. For example, but not limited to, indicia 110 can be in the form of type printed information that provides information relating to the intraocular lens that can include product type, serial number, product number, optical parameters of the lens such as the optical power of the lens, and/or dimensional measurements of the optic of the lens and/or the overall length of the lens itself. Additionally, the indicia 110 can be represented by a barcode. In that regard, a barcode scanner can electronically read the barcode to determine all of the type printed information on the upper surface 108 of the lens.

It should be noted, that the barcode may contain additional information relating to the intraocular lens being held by holder 100 that is not also printed on the upper surface 108 of the holder. For example, the barcode information can provide additional information relating to the manufacturing of the lens such as the facility used to manufacture the lens, machinery used to manufacture lens, and/or materials used in manufacturing the lens.

Although not shown, it is contemplated that the indicia 110 can contain information relating to the packaging and shipping of an intraocular lens being held by lens holder 100. In that regard, the type printed information and/or barcode on lens holder 100 can provide information relating to the packaging and shipping of an intraocular lens being held by lens holder 100 to a specified end user (e.g. healthcare provider). Therefore, as will be described in more detail below, lens holder 100 provides the capability for an intraocular lens to remain within the lens holder 100 for the purposes of manufacturing, packaging, and shipping of the intraocular lens to a specified end user.

Additionally, upper surface 106 has indexing features 112, or notches, that extend through upper surface 106 to lower surface 108. In that regard, when lens holder 100 is assembled, indexes 112 can be used to properly align and/or interface lens holder 100 with a manufacturing machine. In other words, indexes 112 provide a means for lens holder 100 to be properly positioned with respect to a manufacturing machine such that the intraocular lens being held by the holder is properly processed by the manufacturing machine. Additionally, indexes 112 provide a means for lens holder 100 to be properly positioned with respect to a packaging and/or shipping machine such that the holder and the lens being held by the holder are properly processed by the packaging and/or shipping machine.

It should be noted that indexes 112 can be incorporated into either of upper member 104 and lower member 104. For example, indexes 112 can be incorporated into only upper member 102 or lower member 104. Alternatively, for example, indexes 112 can be incorporated into both the upper member 102 and lower member 104. Furthermore, even though only a pair of indexes 112 has been shown with respect to upper member 102, it is contemplated that one or more than two indexes can be disposed on or through either upper member 102 or lower member 104.

With reference to FIG. 2, a perspective view of upper member 102 of lens holder 100 is shown. Upper member 102 has a base portion 114 that extends axially from the lower surface 108. Base portion 114 has an exterior surface 116. As shown, base portion 114 has a pair of projections 118 that extend radially from the exterior surface 116. Projections 118 are substantially disposed 180° from one another about the exterior surface 116 of base portion 114. In other words, projections 118 are aligned with one another and are substantially disposed on opposite sides of base portion 114.

Base portion 114 has an end surface 120 that has a swept helical shape. As shown, an apex 122 of each of the concave portions of the end surface 120 is substantially aligned with projections 118. Furthermore, an apex 124 of each of the convex portions of the end surface 120 is substantially disposed 180° from one another. Thus, apexes 122 of the concave portions of the end surface 120 are spaced approximately 90° from the apexes 124 of the convex portions of the end surface 120.

Referencing FIGS. 1 and 2, upper member 102 also has an axial bore 126 extending from the upper surface 106 through an opening 128 of base portion 114. Axial bore 126 is central disposed within upper member 102. FIG. 3 shows a cross-section view of the side view of upper member 102. As shown in FIG. 3, axial bore 126 is defined by a surface 130. Surface 130 has a first cylindrical portion 132 and a second conical portion 134. First cylindrical portion 132 is substantially parallel to a longitudinal axis $L_1$ of axial bore 126. Second conical portion 134 is tapered, or sloped, such that axial bore 126 is conical shape along the section defined by second portion 134. The first portion 132 and the second conical portion 134 are joined by a transition portion 133 concentrically disposed about the longitudinal axis $L_1$. Additionally, second portion 134 extends at angle 136 from the upper surface 106 of upper member 102. Here angle 136 is approximately 60°. However, it is contemplated that angle 136 can be greater than or less than 60°. For example, in other embodiments, angle 136 can range from about 10° to about 80°. Further, the angle can be defined in relation to the longitudinal axis $L_1$. In the illustrated embodiment, the second conical portion 134 extends at an angle of 30° to define a truncated cone.

In the present embodiment, this tapered bore is designed to aid or assist in the removal of bubbles that may collect during submersion into an optical solution that may be used during optical measurements. It has been found that when angle 136 is about 60° it produces the beneficial and unexpected result of reducing and/or preventing the formation of bubbles within lens holder 100 when the holder is submerged in an optical solution. For example, the conical or sloped shape of axial bore 126 defined by second conical portion 134 has been found to aid or assist in the removal of bubbles when lens holder 100 is vertically submerged within an optical solution. In that regard, when lens holder 100 is vertically submerged in an optical solution the sloped or tapered second conical portion 134 encourages bubbles to disperse, or roll, along the tapered surface and thereby remove bubbles from lens holder 100. Thus, because of the reduction and/or prevention of bubbles and/or particulate better optical and/or dimensional measurements can be taken during the manufacturing process of a lens held by holder 100.

Additionally, as best seen in FIG. 1, upper member 102 has a plurality of indentations 138 along its outer surface. Indentations 138 provide a gripping surface for use by a machine during the manufacturing process and/or a user of lens holder 100 (e.g. healthcare provider). Additionally, as will be described in greater detail bellow, indentations 138 provide a gripping surface such that the upper member can be rotated about its axis relative to lower member 104 to engage and lock the two members together to form lens holder 100.

FIG. 4 is a perspective view of lower member 104 of the lens holder 100. Lower member 104 has an upper surface 140 and an opposing lower surface 142. Extending axially from the upper surface 140 is a receiving member 144. Receiving member 144 is disposed centrally on upper surface 140. As will be described in greater detail below, among other things, receiving member 144 defines a cavity 146 for receiving base portion 114 of upper member 102 in order to lock the upper member 102 and lower member 104 together to form lens holder 100.

Receiving member 144 has a pair of spring lever arms 148, or coupling member. Spring lever arms 148 are biased downward towards upper surface 140 of lower member 104. Each of the respective ends of the spring lever arms define a lip 150 and a recess 152. Adjacent the spring lever arms 148 are slots 154 that define access to channels 156 that are located below the spring lever arms 148. Because of slots 154 and channels 156 the pair of spring lever arms 148 are resiliently flexible. In that regard, the arms can be positioned away from upper surface 140 of lower member 104 when a force is applied to move the arms in that direction, but are resilient in attempting to resume their downward biased position as shown in FIG. 4. As will be described in greater detail below, lip 150 and recess 152 of spring lever arms 148 are sized and shaped to receive projections 118 of base portion 114 in order to lock the upper member 102 to the lower member 104.

Additionally, receiving member 144 has a floor 158 that has troughs 160a-c, or channels, formed within floor 158. In other words, troughs 160a-c are recessed with respect to floor 158. As shown in FIG. 4, troughs 160a-c are parallel to each other and extend substantially transverse to axis $L_2$ of lower member 104. Moreover, troughs 160a-c extend substantially across floor 158 such that receiving member 144 is interrupted by troughs 158. The interruption of receiving member 144 by troughs 160a-c defines unobstructed passageways into cavity 144. As will be described in greater detail below, troughs 160a-c allow for dimensional measurements to be obtained on an intraocular lens being held by lens holder 100 during the manufacturing process.

Furthermore, floor 158 has prongs 162a-d, or posts, that are designed to receive haptics of an intraocular lens disposed within cavity 146. In that regard, prongs 162a-d are shown as being grouped in pairs on opposing sides of receiving member 146. Prongs 162a-d are designed such that the haptics of an intraocular lens can be disposed between the respective pairs of prongs 162a-d. In other words, prongs 162a-d act as an alignment guide to position and hold the intraocular lens within cavity 146 of receiving member 144 at a predefined position.

It should be noted that prongs 162a-d can assume any shape to better accommodate and match the curvature of any haptic and/or lens optic disposed within cavity 146. Furthermore, although shown in the exemplary embodiment as groups of two pairs of prongs, it is contemplated that more or less than two pair of prongs can be used to position and align an intraocular lens within cavity 146 of receiving member 144.

Additionally, floor 158 of receiving member 144 is interrupted by an axial bore 164. As best shown in FIG. 5, which is a cross-section view of a side view of the lower member 104, axial bore 164 extends from cavity 146 through lower surface 142 of lower member 104. Axial bore 164 is centrally disposed through lower member 104 and is defined by a surface 166.

Surface 166 has a first cylindrical portion 168 and a second conical portion 170. First cylindrical portion 168 is substantially parallel to a longitudinal axis $L_2$ of axial bore 164. Second conical portion 170 is tapered, or sloped, such that axial bore 164 is conical shape along the section defined by second portion 170. The first cylindrical portion 168 and the second conical portion 170 are joined by a transition portion 169 concentrically disposed about the longitudinal axis $L_2$. Additionally, second conical portion 170 extends at angle 172 from the lower surface 142 of lower member 104. Here angle 172 is approximately 60°. However, it is contemplated that angle 172 can be greater than or less than 60° relative to the lower surface 142 of lower member 104. For example, in other embodiments, angle 172 can range from about 10° to about 80°. Further, the angle can be defined in relation to the longitudinal axis $L_2$. In the illustrated embodiment, the second conical portion 170 extends at an angle of 30° to define a truncated cone.

In the present embodiment, it has been found that when angle 172 is about 60° this produces the beneficial and unexpected result of reducing and/or preventing the formation of bubbles within lens holder 100 when the holder is submerged in an optical solution. For example, the conical or sloped shape of axial bore 164 defined by second conical portion 170 has been found to aid or assist in the removal of bubbles when lens holder 100 is vertically submerged within an optical solution. In that regard, when lens holder 100 is vertically submerged in an optical solution the sloped or tapered second conical portion 170 encourages bubbles to disperse, or roll, along the tapered surface and thereby remove bubbles from lens holder 100. Thus, because of the reduction and/or prevention of bubbles and/or particulate better optical and/or dimensional measurements can be taken during the manufacturing process of a lens held by holder 100.

Similar to upper member 102, the lower member 104 also has various indexing features. For example, as shown in FIG. 4, lower member 104 has apertures 174 and ribs 176 that can act as indexing features during the manufacturing process. In that regard, when lens holder 100 is assembled, apertures 174 and ribs 176 can be used to properly align and/or interface holder 100 with a manufacturing machine. In other words, apertures 174 and ribs 176 provide a means for lens holder 100 to be properly positioned with respect to a manufacturing machine such that the intraocular lens being held by the holder is properly processed by the manufacturing machine. Additionally, apertures 174 and ribs 176 provide a means for lens holder 100 to be properly positioned with respect to a packaging and/or shipping machine such that the holder and the lens being held by the holder are properly processed by the packaging and/or shipping machine.

It should be noted that the indexing features disclosed herein, including the apertures 174 and ribs 176, can be incorporated into either of upper member 104 and lower member 104. For example, the indexing features can be incorporated into only upper member 102 or lower member 104. Alternatively, for example, the indexing features can be incorporated into both the upper member 102 and lower member 104. Furthermore, even though only a pair of apertures 174 and ribs 176, respectively, have been shown with respect to lower member 104, it is contemplated that one or more than two apertures 174 and ribs 176, respectively, can be disposed on or through either upper member 102 or lower member 104.

Additionally, as best seen in FIG. 4, lower member 104 has a plurality of indentations 178 along its outer surface. Indentations 178 provide a gripping surface for use by a machine during the manufacturing process such that the machine can grip and hold the lens holder 100. Additionally, as will be described in greater detail bellow, indentations 178 provide a gripping surface for either a healthcare provider (e.g. end user) and/or a manufacturing machine to allow for the lower member 104 to be rotated about its axis relative to upper member 102 to engage and either lock or unlock the two members relative to each other.

Figure 6:
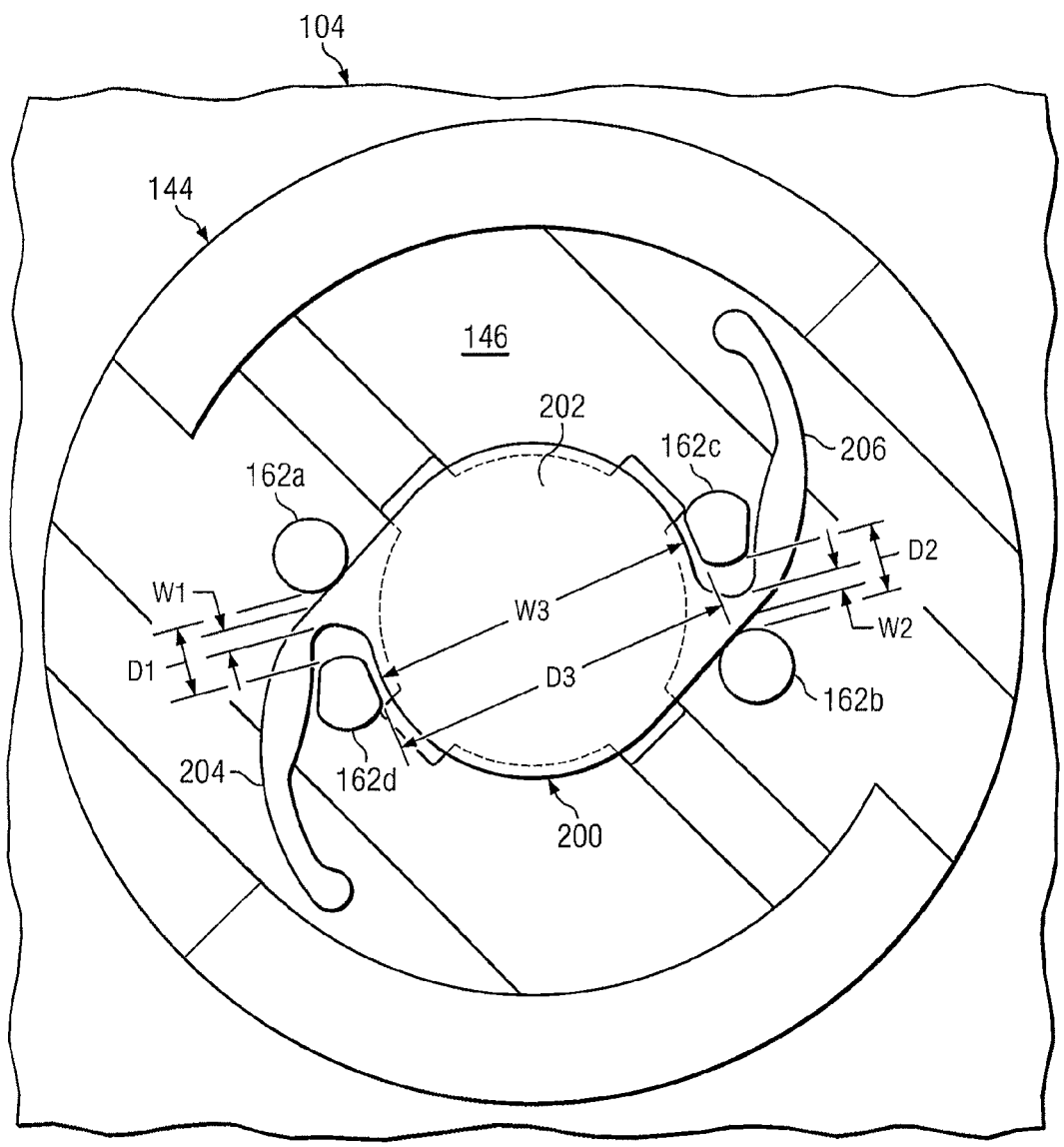
FIG. 6 is a partial overhead view of the lower member of FIG. 4 with an intraocular lens disposed within the lower member.

The assembly of lens holder 100 begins with the placement of an intraocular lens within lower member 104. FIG. 6 shows an overhead view of the lower member 104 receiving an intraocular lens 200. Intraocular lens 200 is shown as being a single piece intraocular lens. However, lens holder 100 can also be used with multi-piece intraocular lenses. Therefore, in alternative embodiments, intraocular lens 200 can be a multi-piece intraocular lens.

Intraocular lens 200 has a lens optic 202 and haptics 204 and 206 that are connected to the lens optic 202 to form a uniform single piece intraocular lens. As shown in FIG. 6, intraocular lens 200 is received within cavity 146 of receiving member 144. More specifically, prongs 162*a-d* act as alignment guides to position and hold the intraocular lens within cavity 146. In that regard, prongs 162*a-d* centrally position the lens optic 202 over axial bore 164 and trough 160*b*. Additionally prongs 162*a-d* act to position at least a portion of haptics 204 and 206 over troughs 160*a* and 160*c*, respectively.

As shown in FIG. 6, haptic 204 of intraocular lens 200 is positioned between prongs 162*a* and 162*d* and haptic 206 is positioned between prongs 162*b* and 162*c*. In that regard, prongs 162*a* and 162*d* are spaced apart from each other a distance $D_1$ such that a width $W_1$ of haptic 204 positioned between the prongs is less than the distance $D_1$. Similarly, prongs 162*b* and 162*c* are spaced apart from each other a distance $D_2$ such that a width $W_2$ of haptic 206 positioned between the prongs is less than the distance $D_2$. Because prongs 162*a-d* are spaced apart from one another a greater distance than the width of the haptic being positioned between the prongs, one can more easily align and position the intraocular lens 200 between the prongs 162*a-d*. Additionally, the spatial arrangement of prongs 162*a-d* allows the intraocular lens 200 to be rotated about the lens's longitudinal axis approximately by the delta between distance $D_1$ and width $W_1$ and/or distance $D_2$ and width $W_2$. As will be discussed in more detail below, the rotational movement of intraocular lens 200 is prevented when the upper member 102 and lower member 104 are locked together.

Furthermore, as shown in FIG. 6, lens optic 202 has a width $W_3$ which is less than a distance $D_3$ between prong 162*c* and 162*d*. As such, the lens is allowed some movement along an axis that is substantially parallel to the floor 158 of receiving member 144 when the haptics 204 and 206 are positioned between prongs 162*a-d*. In that regard, the intraocular lens 200 can be moved along an axis that is substantially parallel to the floor 158 approximately by the delta between width $W_3$ and distance $D_3$. Again, the spatial relationship between prongs 162*c* and 162*d* allows for easier alignment and positioning of the intraocular lens 200 between prongs 162*a-d*.

As discussed above, prongs 162*a-d* are designed to act as an alignment guide to position and hold the intraocular lens within cavity 146 of receiving member 144. In that regard, prongs 162*a* and 162*b* have a circular cross-sectional shape while prongs 162*c* and 162*d* have a rounded trapezoidal cross-sectional shape. The circular cross-sectional shape of prongs 162*a* and 162*b* allow for a slidable interface surface for haptics 204 and 206 when the upper member 102 and lower member 104 are unlocked with respect to each other. Moreover, the rounded trapezoidal cross-sectional shape of prongs 162*c* and 162*d* allows for an accommodating fit that corresponds to the contours of the lens optic 202 and/or haptics 204 and 206 when intraocular lens 200 is positioned between prongs 162*a-d*.

In alternative embodiments, prongs 162*a-d* can have alternative cross-sectional shapes. For example, prongs 162*c* and 162*d* can have a circular cross-sectional shape while prongs 162*a* and 162*b* can have a rounded trapezoidal cross-sectional shape. Additionally, in other embodiments prongs 162*a-d* can assume any cross-sectional shape to better accommodate and/or match the contours of the haptics 204 and 206 and/or the lens optic 202. Moreover, in other alternative embodiments the spatial relationship of prongs 162*a-d* in relation to intraocular lens 200 can be such that the intraocular lens 200 is prohibited from any movement when positioned between prongs 162*a-d*.

Figure 7:
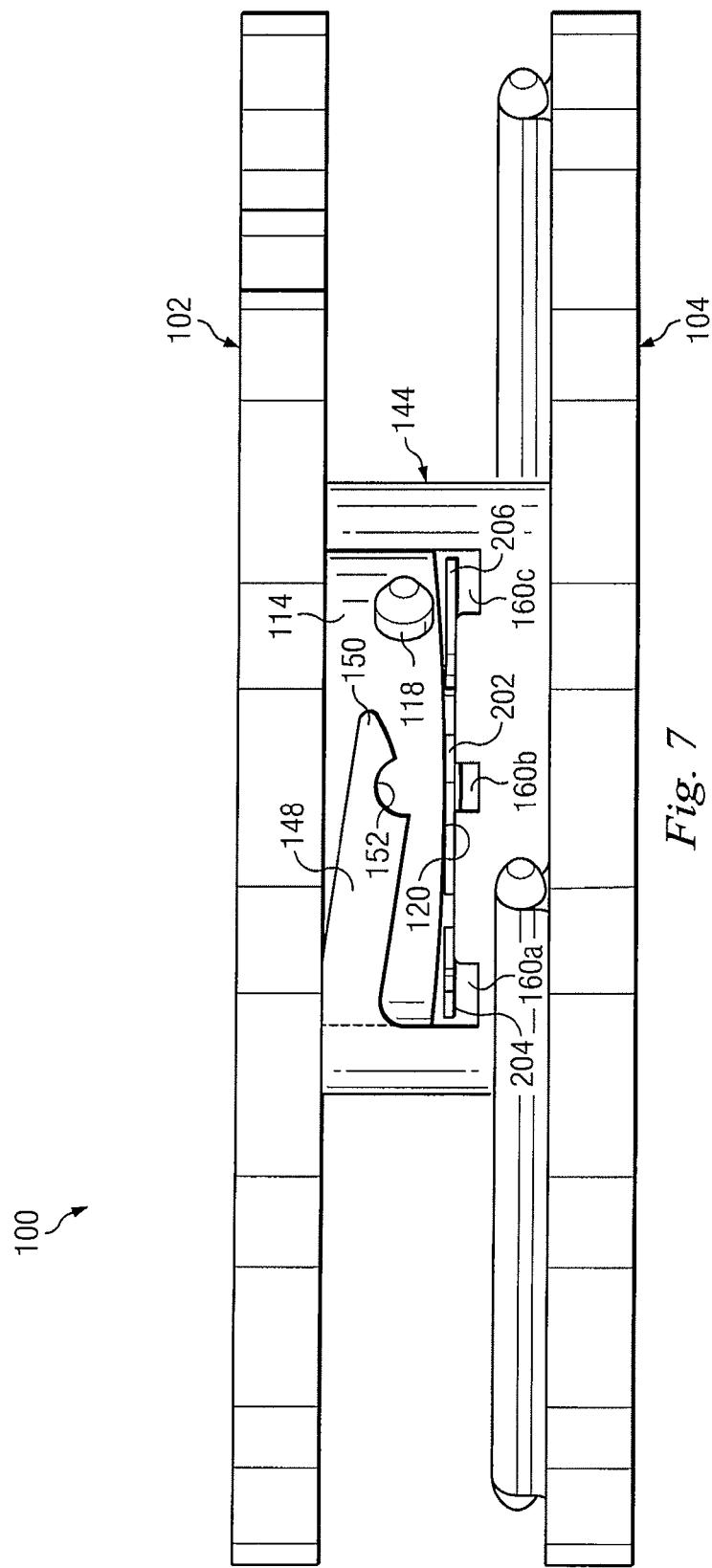
FIG. 7 is a side view of the lens holder of FIG. 1 in an unlocked configuration with the intraocular lens of FIG. 6 disposed within the lens holder.

After placement of intraocular lens 202 within cavity 146 of lower member 104, the upper member 102 is positioned adjacent lower member 104. FIG. 7, shows a side view of the upper member 102 positioned adjacent the lower member 104 in an unlocked position, or unlocked configuration. As shown, when lens holder 100 is in the unlocked position upper member 102 is positioned such that base portion 114 is disposed within cavity 146 of receiving member 144 of lower member 104. More specifically, upper member 102 is positioned such that projections 118 of base portion 114 are disposed within slots 154. The upper member 102 and lower member 104 can be separated from one another by axial movement of the members away from each other.

In the unlocked position, the end surface 120 of base portion 114 is positioned such that the concave portions of the end surface 120 are substantially disposed over troughs 160a and 160c. Additionally, in the unlocked position, the convex portions of end surface 120 are substantially disposed over trough 160b. Thus, as shown in FIG. 7, when lens holder 100 is in the unlocked position end surface 120 does not engage or contact intraocular lens 200 disposed within receiving member 144 of lower member 104. In other words, the end surface 120 does not engage or contact the portions of haptics 204 and 206 that are disposed over troughs 160a and 160b.

Figure 8:
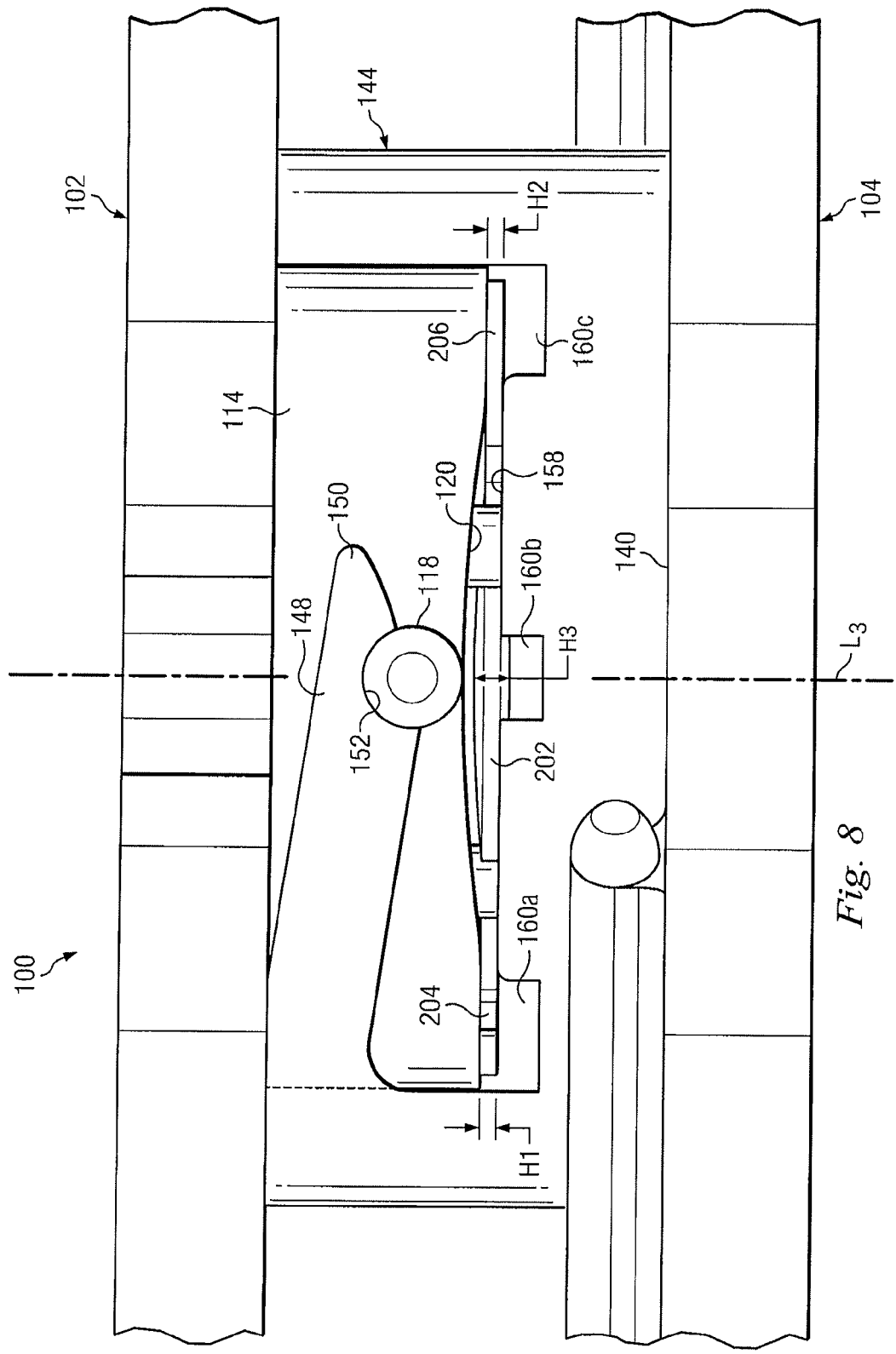
FIG. 8 is a partial side view of the lens holder of FIG. 1 in a locked configuration with the intraocular lens of FIG. 6 disposed within the lens holder.

FIG. 8 shows the side view of lens holder 100 in a locked position, or locked configuration. To change the configuration of lens holder 100 from the unlocked position, as shown in FIG. 7, to a locked configuration, as shown in FIG. 8, the upper member 102 and lower member are rotated relative to each other about longitudinal axis $L_3$ of lens holder 100. For example, a machine and/or end user can grasp indentations 138 on the upper member 102 and indentations 178 on the lower member 104 and twist or rotate the two members relative to each other about longitudinal axis $L_3$. Alternatively, the machine and/or end user can grasp indentations 138 on the upper member 102 and indentations 178 on the lower member 104 and twist or rotate only one of the two members while keeping the other member stationary in order to lock lens holder 100.

When the upper member 102 and lower member 104 are rotated relative to each other the lip portions 150 of spring lever arms 148 slides along projections 118 of base portion 114 such that the arms 148 are flexed axially away from upper surface 140 of the lower member 104. This flexion of spring lever arms 148 allows the projections 118 of base portion 114 to be slidably received within recesses 152 of arms 148. The reception of projections 118 within their respective recesses 152 causes the spring lever arms 148 to return to their normal biased downward positioned thereby locking the projections 118 within recess 152. Additionally, the lip 150 of spring lever arms 148 prevents rotation of the upper member 102 relative to the lower member 104 once the lens holder 100 has assumed the locked position. In that regard, lips 150 act as an abutment surface against projections 118 thereby preventing the projection 118 from being forced out of recess 152 without the required force being applied to overcome the downward biased of the spring lever arms 148 in order to unlock the upper member 102 from the lower member 104.

As shown in FIG. 8, when lens holder 100 is in the locked position end surface 120 engages or contacts intraocular lens 200 disposed within receiving member 144 of lower member 104. In the locked position, the end surface 120 of base portion 114 is positioned such that the apexes 124 of convex portions of the end surface 120 are substantially disposed over troughs 160a and 160c. Additionally, in the locked position, the apexes 122 of the concave portions of the end surface 120 are substantially disposed over the of the portion trough 160b. Moreover, apexes 124 of the convex portions of the end surface 120 engage or contact the portions of haptics 204 and 206 that are disposed over troughs 160a and 160c. Specifically, at least a portion of the haptics 204 and 206 are deflected by the convex portions of end surface 120 in the direction of troughs 160a and 160c, respectively. Because of the deflection of haptics 204 and 206 towards troughs 160a and 160c, respectively, the haptics are held stationary by a frictional fit formed between the convex portions of the end surface 120 contacting the haptics and the floor 158 that contacts the haptics. Thus, when lens holder 100 is in the locked position, intraocular lens 200 is secured within the holder such that intraocular lens 200 is stationary. In other words, intraocular lens 200 is prevented from movement within holder 100 when the upper member 102 is locked with the lower member 404.

During the manufacturing and packaging processes lens holder 100 can be positioned horizontally, vertically, diagonally, and/or any other angle with respect to a manufacturing and/or packaging machine. Regardless of the orientation of lens holder 100 with respect to a given manufacturing and/or packaging machine, intraocular lens 200 remains secured within lens holder 100 because of the frictional fit formed between the convex portions of the end surface 120 contacting the haptics 204 and 206 and the floor 158 of the receiving member 144 that contacts the haptics 204 and 206. Thus, the intraocular lens remains stationary within lens holder 100 allowing for increased precision and accuracy during the manufacturing of the lens.

Moreover, as shown in FIG. 8, lens holder 100 allows for dimensional measurements of intraocular lens 200 to be obtained when the holder is in the locked position. In that regard, because at least a portion of the haptics 204 and 206 are deflected by the convex portions of end surface 120 into troughs 160a and 160c, lens holder 100 allows for unobstructed dimensional measurement to be taken of haptics 204 and 206. For example, the unobstructed passageway created by trough 160a for haptic 204 and trough 160c for haptic 206 allow for a height $H_1$ for haptic 204 and a height $H_2$ for haptic 206 to be obtained during the manufacturing process. In other words, lens holder 100 allows for dimensional measurements to be taken of optic haptics 204 and 206 at angle substantially transverse to axis $L_3$ of lens holder 100 because of the unobstructed side passageways into lens holder 100 that are created by troughs 160a and 160c.

Additionally, dimensional measurements can be obtained for lens optic 202 during the manufacturing process. More specifically, because the apexes 122 of the concave portions of end surface 120 are substantially disposed over trough 160b when lens holder 100 is in the locked position, the lens optics 202 is unobstructed. In other words, the positing of the apexes 122 over trough 160b creates a space between the end surface 120 and the lens optics 202. In that regard, a height measurement $H_3$ of lens optic 202 can be taken because of the unobstructed passageway created by the combination of trough 160b and the concave portions of end surface 120. Thus, lens holder 100 allows for dimensional measurements to be taken of lens optic 202 at angle substantially transverse to axis $L_3$ of lens holder 100 because of the unobstructed side passageways into lens holder 100 that are created by trough 160b and the concave portions of end surface 120.

Figure 9:
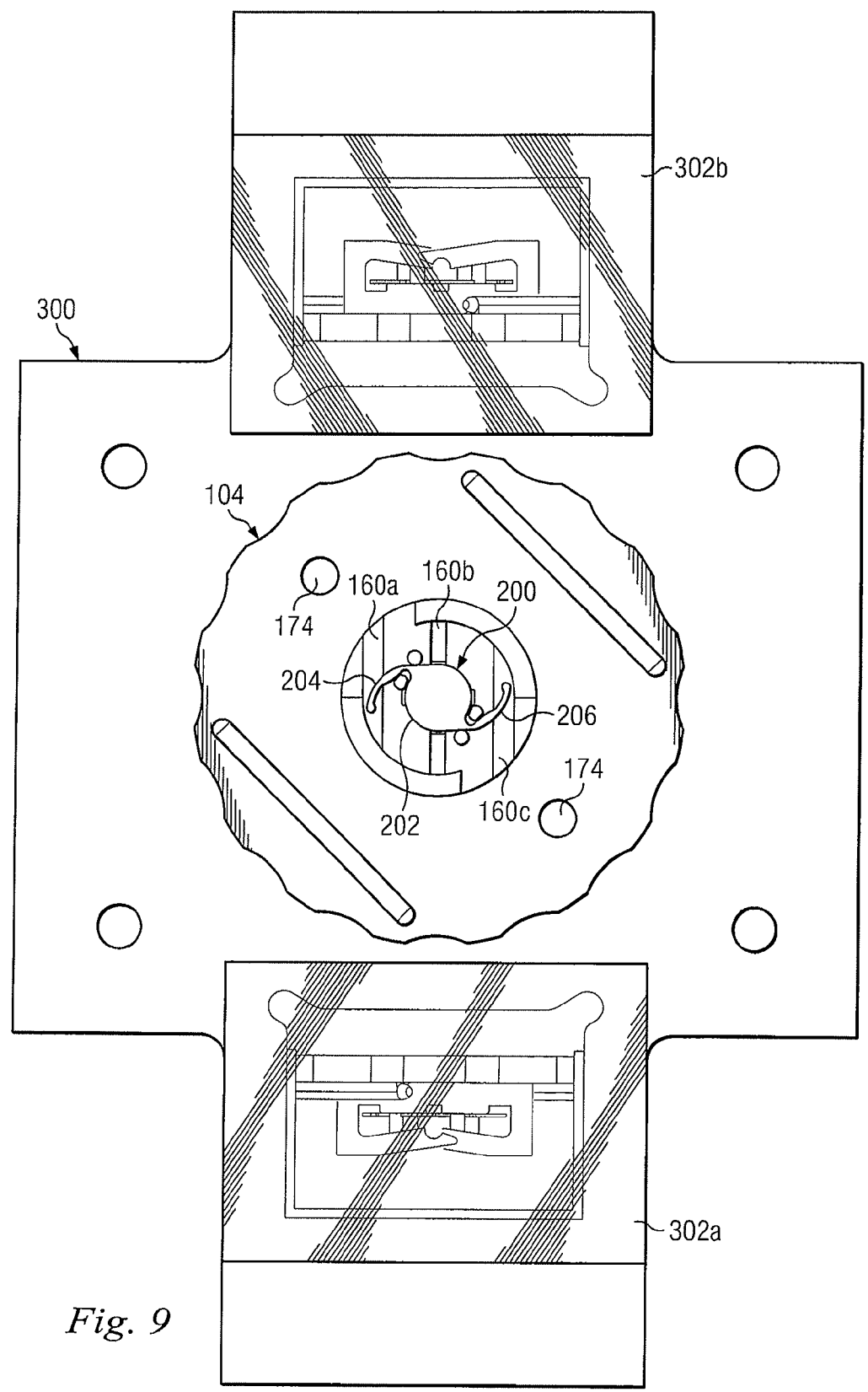
FIG. 9 is an overhead view of the lens holder of FIG. 8 with the upper member removed for clarity purposes being held by an exemplary manufacturing machine.

FIG. 9 shows lens holder 100 with upper member 102 removed for clarity purposes being held by an exemplary manufacturing machine 300. As shown, lens holder 100 is properly positioned and aligned with a platform of machine 300 by using apertures 174 of lower member 104 as indexing features. Machine 300 has optical reflective surfaces 302a and 302b that can be used to obtain dimensional measurements of the intraocular lens 200 being held by lens holder 100. As shown, optical reflective surfaces 302a and 302b have a reflective surface, for example an optical mirror, which can be used by a component of machine 300 (e.g. photographic device or light source), or separate machine, to obtain dimensional measurements of intraocular lens 200 being held by lens holder 100. In other words, because of troughs 160a-c of lens holder 100, one can obtain side dimensional measurements of intraocular lens 200 from a photographic device positioned over lens holder 100 by using optical reflective surfaces 302a and 302b.

In that regard, as discussed above and as shown in FIG. 9, troughs 160a and 160c allow machine 300 to have an unobstructed view of at least a portion of haptics 204 and 206. Additionally, trough 160b in combination with the space created between lens optic 202 and end surface 120 by positioning the concave portions of end surface 120 over trough 160b allows machine 300 to have an unobstructed view of lens optic 202 of intraocular lens 200. Therefore, when lens holder 100 is in the locked position machine 300 can obtain dimensional measurements of lens optic 202 and haptics 204 and 206.

Figure 10:
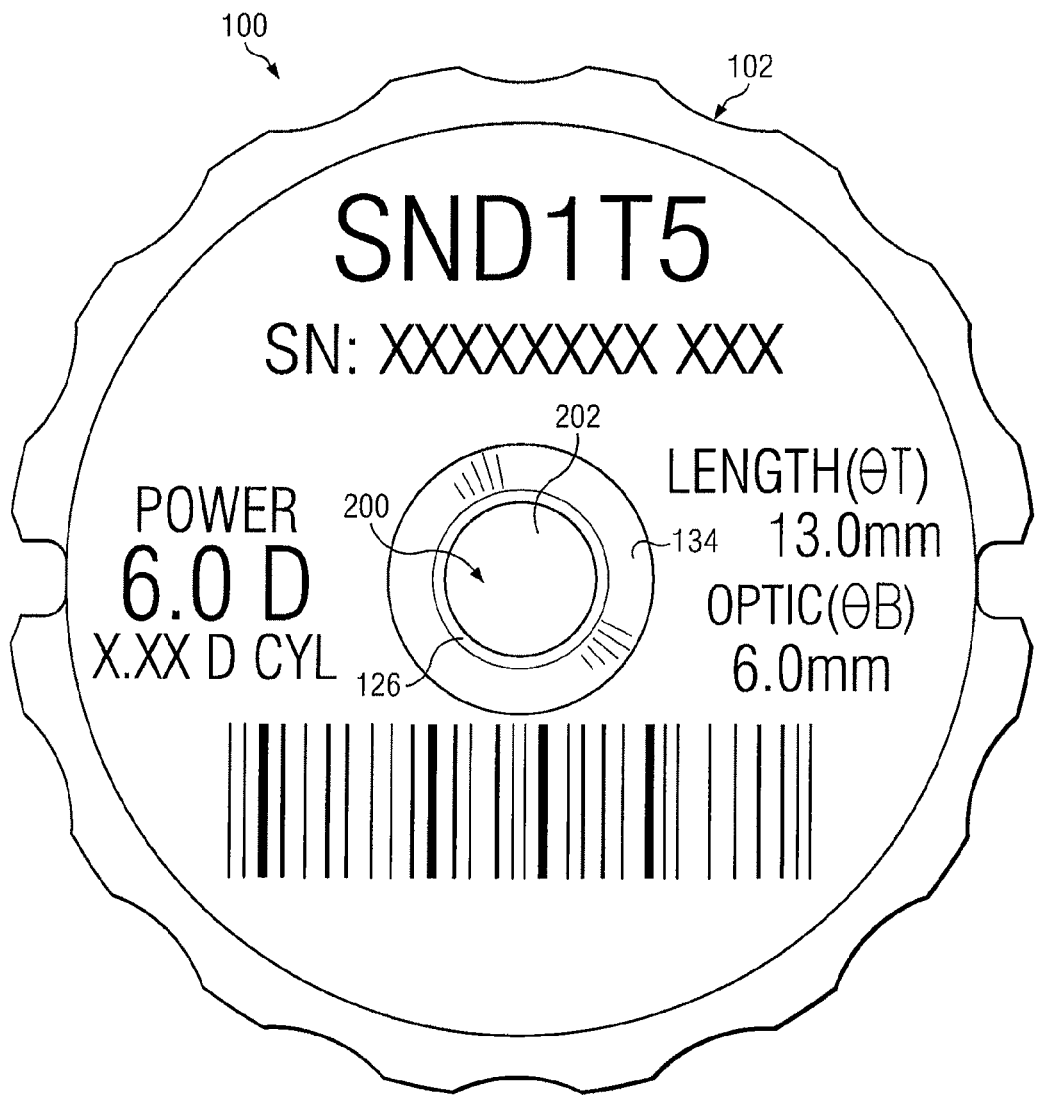
FIG. 10 is an overhead view of the lens holder of FIG. 8 with the intraocular lens of FIG. 6 disposed within the lens holder.

FIG. 10 is an overhead view of lens holder 100 with the intraocular lens 200 disposed within the lens holder. As shown, axial bore 126 allows for optical measurements of lens optic 202 of intraocular lens 200 to be obtained during the manufacturing process. Although not shown in FIG. 10, axial bore 164 allows for optical measurements of lens optic 202 of intraocular lens 200 to be taken through the lower member 104 during the manufacturing process as well.

Additionally, during the manufacturing process axial bores 126 and 164 allow for the lens holder 100 to be submerged into an optical solution for the purpose of optical measurements. As discussed above, these axial bores are defined by sloped surfaces that give the bores a conical shape. In that regard, the conical shape of axial bores 126 and 164 reduces and/or prevents the formation of bubbles when submerged in the optical solution for optical measurements.

Furthermore, during the manufacturing process axial bores 126 and 164 allow for easier delivery and removal of various solutions (e.g. cleaning solutions, etc.) with respect to lens holder 100. In that regard, because of the conical shape of axial bores 126 and 164 their respective diameters are larger near upper surface 106 and lower surface 142, respectively, than as compared to the remaining diameter of the respective bores. These larger diameters near upper surface 106 and lower surface 142 allow for easier introduction of solutions, such as cleaning solutions, into lens holder 100 while also enabling for easier removal of the solutions from lens holder 100.

As discussed above, lens holder 100 provides protection for the lens while allowing for optical and dimensional measurement to be taken during the manufacturing process. Additionally, lens holder 100 can be used as the packaging and shipping container for intraocular lens 200. In that regard, intraocular lens 200 can remain within the same lens holder 100 during the manufacturing, packaging, and shipping processes. In other words, the lens holder received by an end user, such as a healthcare provider, is the same holder that was used to protect and hold the lens during the manufacturing, packaging, and shipping of the intraocular lens to the end user. Thus, potential damage that may occur from transferring the lens to a separate lens holder that is used to package and ship the lens to a healthcare provider can be avoided by using lens holder 100. Additionally, by using the same lens holder during manufacturing, packaging, and shipping the complexity of the manufacturing, packaging, and shipping processes are reduced.

Figure 11:
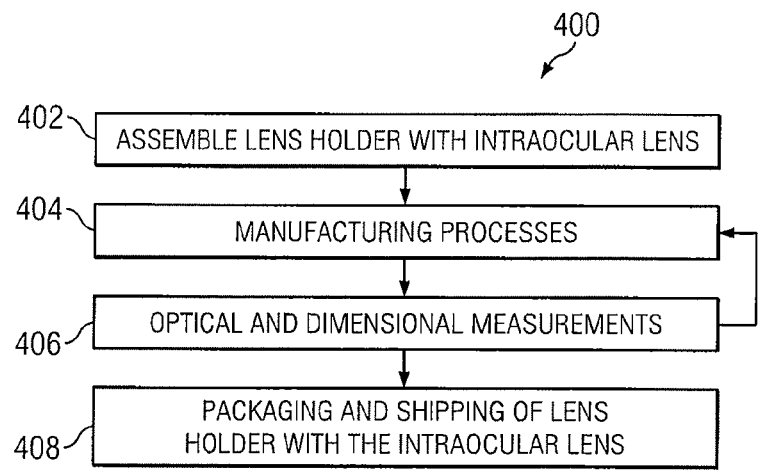
FIG. 11 discloses a method of processing an intraocular lens using the lens holder of FIG. 1.

FIG. 11 discloses a method 400 of processing intraocular lens 200 using lens holder 100. The method begins at step 402 in which intraocular lens 200 is positioned within lens holder 100 and the lens holder 100 is locked, as discussed above with reference to FIGS. 6-8. Next, step 404 represents the various manufacturing processes that occur during the manufacturing of intraocular lens 200. One skilled in the art recognizes the various manufacturing process required to manufacture intraocular lens 200.

As discussed above, lens holder 100 has various indexing features that can be used to properly align and/or interface lens holder 100 with a manufacturing and/or packaging machine. Thus, during each step of method 400, the indexing features of lens holder 100 allow for the intraocular lens 200 being held by lens holder 100 to be properly processed by the manufacturing and/or packaging machine.

During step 406, various optical and dimensional measurements are taken in-process during the manufacturing of intraocular lens 200. As discussed above with respect to FIGS. 8-10, during the manufacturing process lens holder 100 allows for dimensional measurements of intraocular lens 200 to be taken in part because of troughs 160a-c. In other words, lens holder 100 allows for dimensional measurements to be taken of optic lens 202 and haptics 204 and 206 at angle substantially transverse to axis $L_3$ because troughs 160a-c create unobstructed side passageways into lens holder 100. Furthermore, lens holder 100 allows for optical measurements of the lens optic 202 to be taken through axial bores 126 and 164.

These measurements taken during step 406 can be used in subsequent manufacturing processes to further refine intraocular lens 200 to ensure that the lens meet a specified design requirement. Accordingly, if further manufacturing processes are required after the taking of optical and dimensional measurements the method returns to step 404 for further manufacturing process of the intraocular lens. However, if after taking the optical and dimensional measurements it is determined that the lens meets the specified design requirements, then the method can continue to step 408.

At step 408, lens holder 100 while still holding intraocular lens 200 is used as the packaging material for shipping the intraocular lens to a designated end user. Additionally, during step 408, for example, lens holder 100 while still holding intraocular lens 200 may further be packaged by placing the lens holder 100 within a tie-back pouch and sealed within the pouch. Thus, during step 412, the lens holder 100 remains locked such that the intraocular lens is not removed from the holder. As discussed above, potential damage that might occur to intraocular lens 200 if the lens were transferred from lens holder 100 to another lens holder that is used to package and ship the lens can be avoided because of the use of lens holder 100 as the packaging holder for the lens. Therefore, during step 412, lens holder 100 acts as the packaging material for intraocular lens 200 and can be labeled with appropriate shipping information such that the intraocular lens is shipped to the appropriate end user (e.g. healthcare provider).

It should be noted that method 400 provides a method for processing an intraocular lens in which the intraocular lens remains within lens holder 100 throughout the disclosed method. In other words, intraocular lens 200 remains locked within the same lens holder 100 during the manufacturing, packaging, and shipping processes described with respect to method 400. Therefore, the lens holder 100 received by an end user, such as a healthcare provider, is the same holder that was used to protect and hold the lens during the manufacturing, packaging, and shipping of the intraocular lens to the end user. Thus, by using the same lens holder during the manufacturing, packaging, and shipping processes the complexity of manufacturing, packaging, and shipping the intraocular lens is reduced as well as potential damage that might occur from transferring the intraocular lens 200 to a separate lens holder during the various processes is avoided altogether.

The lens holders disclosed herein are in whole or in part may be constructed of biocompatible materials of various types including metals or polymers. For example, but not by way of limitation, the lens holder can be constructed in whole or in part of polypropylene. In such a scenario, the lens holder can be constructed in whole or in part of polypropylene FP-300-F.

While the present invention has been illustrated by the above description of embodiments, and while the embodiments have been described in some detail, it is not the intention of the applicant to restrict or in any way limit the scope of the invention to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general or inventive concept. It is understood that all spatial references, such as "longitudinal axis," "horizontal," "vertical," "diagonal," "top," "upper," "lower," "bottom," "left," and "right," are for illustrative purposes only and can be varied within the scope of the disclosure.

What is claimed is:

1. A holder for an intraocular lens, the holder comprising:
   an upper member having a base portion extending from the upper member along a first longitudinal axis; and
   a lower member having a receiving member defining a cavity for receiving the intraocular lens and a coupling member for engaging the base portion, the receiving member extending from the lower member along a second longitudinal axis and having at least one channel extending substantially through the receiving member that is substantially transverse to the second longitudinal axis,
   wherein the holder has a locked position such that the upper and lower members are locked with respect to each other and the at least one channel provides unobstructed access into the cavity of the receiving member for obtaining a dimensional measurement of the intraocular lens when the holder is in the locked position;
   wherein the upper member has a conical shape axial bore extending through the base portion in a direction substantially parallel with the first longitudinal axis, the conical shape axial bore providing an unobstructed access into the cavity of the receiving member for obtaining an optical measurement of the intraocular lens when the holder is in the locked position.

2. The holder of claim 1, wherein the at least one channel provides unobstructed access into the cavity of the receiving member for obtaining the dimensional measurement of a haptic of the intraocular lens.

3. The holder of claim 1, wherein the at least one channel provides unobstructed access into the cavity of the receiving member for obtaining the dimensional measurement of a lens optic of the intraocular lens.

4. The holder of claim 1, wherein the base portion has at least one projection and the coupling member has at least one spring lever arm for receiving the projection to lock the upper and lower members with respect to each other.

5. The holder of claim 1, wherein an end surface of the base portion engages a portion of a haptic of the intraocular lens thereby deflecting the portion of the haptic in the direction of the at least one channel when the holder is in the locked position.

6. The holder of claim 1, wherein the upper member comprises at least one indexing feature comprising at least one rib and/or aperture for use in aligning the holder with a manufacturing machine.

7. The holder of claim 1, wherein the upper member comprises a plurality of indentations along an outer surface to provide a gripping surface on the upper member.

8. A holder for an intraocular lens, the holder comprising:
   an upper member having a base portion extending from the upper member along a first longitudinal axis; and
   a lower member having a receiving member defining a cavity for receiving the intraocular lens and a coupling member for engaging the base portion, the receiving member extending from the lower member along a second longitudinal axis and having at least one channel extending substantially through the receiving member that is substantially transverse to the second longitudinal axis,
   wherein the holder has a locked position such that the upper and lower members are locked with respect to each other and the at least one channel provides unobstructed access into the cavity of the receiving member for obtaining a dimensional measurement of the intraocular lens when the holder is in the locked position;
   wherein the receiving member has a plurality of posts extending from a floor of the receiving member in the direction of the second longitudinal axis, the plurality of posts guide the intraocular lens to a predefined position within the cavity of the receiving member.

9. The holder of claim 8, wherein the at least one channel provides unobstructed access into the cavity of the receiving member for obtaining the dimensional measurement of a haptic of the intraocular lens.

10. The holder of claim 8, wherein the at least one channel provides unobstructed access into the cavity of the receiving member for obtaining the dimensional measurement of a lens optic of the intraocular lens.

11. The holder of claim 8, wherein the base portion has at least one projection and the coupling member has at least one spring lever arm for receiving the projection to lock the upper and lower members with respect to each other.

12. The holder of claim 8, wherein an end surface of the base portion engages a portion of a haptic of the intraocular lens thereby deflecting the portion of the haptic in the direction of the at least one channel when the holder is in the locked position.

13. The holder of claim 8, wherein the upper member comprises at least one indexing feature comprising at least one rib and/or aperture for use in aligning the holder with a manufacturing machine.

14. The holder of claim 8, wherein the upper member comprises a plurality of indentations along an outer surface to provide a gripping surface on the upper member.

15. A holder for an intraocular lens, the holder comprising:
   an upper member having a base portion extending from the upper member along a first longitudinal axis, the base portion including at least one projection extending substantially transverse to the first longitudinal axis; and
   a lower member having a receiving member defining a cavity for receiving the intraocular lens and a coupling member for engaging the base portion, the receiving member extending from the lower member along a second longitudinal axis and having a first and second channel extending substantially through the receiving member that are substantially transverse to the second longitudinal axis, the coupling member having at least one recess for receiving the projection to lock and unlock the upper and lower members with respect to each other,
   wherein when the upper and lower members are locked with respect to each other the first channel provides unobstructed access into the cavity of the receiving member for obtaining a dimensional measurement of a lens optics of the intraocular lens and the second channel provides unobstructed access into the cavity of the receiving member for obtaining a dimensional measurement of a haptic of the intraocular lens;

wherein the base portion has an end surface having at least one concave portion and at least one convex portion;

wherein an apex of the at least one concave portion is substantially disposed over the first channel and an apex of the at least one convex portion is substantially disposed over the second channel when the upper and lower members are locked with respect to each other.

16. The holder of claim 15, wherein the recess is part of a spring lever arm of the receiving member such that reception of the at least one projection within the at least one recess causes the spring lever arm to assume a biased position to lock the upper and lower members with respect to each other.

17. The holder of claim 15, wherein the apex of the at least one convex portion engages a portion of the haptic of the intraocular lens to prevent movement of the intraocular lens within the cavity of the receiving member.

18. The holder of claim 15, wherein the at least one concave portion creates a space between the lens optic and the base portion that is aligned with the first channel when the upper and lower members are locked with respect to each other, the space and the first channel forming the unobstructed access into the cavity of the receiving member for obtaining the dimensional measurement of the lens optics of the intraocular lens.

19. The holder of claim 15, wherein a portion of the at least one convex portion engages a portion of the haptic of the intraocular lens disposed over the second channel thereby deflecting the portion of the haptic in the direction of the second channel when the holder is in the locked position.

20. The holder of claim 15, wherein the upper member comprises at least one indexing feature comprising at least one rib and/or aperture for use in aligning the holder with a manufacturing machine.

* * * * *